United States Patent
Dyba et al.

(10) Patent No.: US 7,646,481 B2
(45) Date of Patent: Jan. 12, 2010

(54) METHOD AND MICROSCOPE FOR HIGH SPATIAL RESOLUTION EXAMINATION OF SAMPLES

(75) Inventors: Marcus Dyba, Mannheim (DE); Hilmar Gugel, Dossenheim (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 373 days.

(21) Appl. No.: 11/623,690

(22) Filed: Jan. 16, 2007

(65) Prior Publication Data

US 2007/0268583 A1   Nov. 22, 2007

Related U.S. Application Data

(60) Provisional application No. 60/853,442, filed on Oct. 23, 2006.

(30) Foreign Application Priority Data

Mar. 1, 2006   (DE) ................. 10 2006 009 833

(51) Int. Cl.
G01J 3/30   (2006.01)

(52) U.S. Cl. .................................... 356/318
(58) Field of Classification Search ............. 356/318
See application file for complete search history.

(56) References Cited

U.S. PATENT DOCUMENTS

| | | | | |
|---|---|---|---|---|
| 4,621,911 A | * | 11/1986 | Lanni et al. | ........... 359/386 |
| 6,055,097 A | * | 4/2000 | Lanni et al. | ........... 359/386 |
| 6,255,642 B1 | * | 7/2001 | Cragg et al. | ........... 250/216 |
| 6,492,638 B2 | | 12/2002 | Hoffmann | |
| 6,555,826 B2 | | 4/2003 | Hoffmann | |

(Continued)

FOREIGN PATENT DOCUMENTS

DE    43 31 570 A1    3/1995

(Continued)

OTHER PUBLICATIONS

S.W. Hell et al., "Imaging and writing at the nanoscale with focused visible light through saturable optical transitions," Applied Physics A, vol. 77, 2003, pp. 859-860.

(Continued)

*Primary Examiner*—Kara E Geisel
(74) *Attorney, Agent, or Firm*—Foley & Lardner LLP

(57) ABSTRACT

A method and a microscope, in particular a laser scanning fluorescence microscope, for high spatial resolution examination of samples, the sample (1) to be examined comprising a substance that can be repeatedly converted from a first state (Z1, A) into a second state (Z2, B), the first and the second states (Z1, A; Z2, B) differing from one another in at least one optical property, comprising the steps that the substance in a sample region (P) to be recorded is firstly brought into the first state (Z1, A), and that the second state (Z2, B) is induced by means of an optical signal (4), spatially delimited subregions being specifically excluded within the sample region (P) to be recorded, are defined in that the optical signal (4) is provided in such a way that a standing wave with defined intensity zero points (5) is formed in the sample region (P) to be recorded.

27 Claims, 4 Drawing Sheets

U.S. PATENT DOCUMENTS

| | | | |
|---|---|---|---|
| 7,064,824 B2 * | 6/2006 | Hell | ............................ 356/317 |
| 7,115,885 B2 | 10/2006 | Hell | |
| 7,224,452 B2 | 5/2007 | Hell | |
| 7,253,893 B2 | 8/2007 | Hell et al. | |
| 7,466,885 B2 | 12/2008 | Gugel | |
| 7,485,875 B2 * | 2/2009 | Wolleschensky et al. | . 250/458.1 |
| 2007/0206276 A1 * | 9/2007 | Gugel et al. | ................. 359/385 |
| 2007/0206277 A1 * | 9/2007 | Gugel et al. | ................. 359/385 |
| 2007/0206278 A1 * | 9/2007 | Dyba et al. | ................. 359/385 |

FOREIGN PATENT DOCUMENTS

| | | |
|---|---|---|
| DE | 100 12 462 A1 | 9/2001 |
| DE | 100 31 458 A1 | 1/2002 |
| DE | 101 18 355 B4 | 10/2002 |
| DE | 101 54 699 A1 | 5/2003 |
| DE | 103 25 459 A1 | 11/2004 |
| DE | 103 25 460 A1 | 11/2004 |
| EP | 1 582 858 A1 | 10/2005 |
| EP | 1 584 918 A2 | 10/2005 |
| WO | WO 2005/024482 A1 | 3/2005 |

OTHER PUBLICATIONS

S. W. Hell et al., "Concepts for nanoscale resolution in fluorescence microscopy," Current Opinion in Neurobiology, vol. 14, 2004, pp. 599-609.

S. W. Hell, "Toward fluorescence nanoscopy," Nature Biotechnology, vol. 21, No. 11, Nov. 2003, pp. 1347-1355.

U.S. Appl. No. 11/653,444, filed Jan. 16, 2007, Gugel et al.
U.S. Appl. No. 11/623,703, filed Jan. 16, 2007, Gugel et al.
U.S. Appl. No. 11/653,446, filed Jan. 16, 2007, Dyba et al.

* cited by examiner

METHOD AND MICROSCOPE FOR HIGH SPATIAL RESOLUTION EXAMINATION OF SAMPLES

CROSS-REFERENCE TO RELATED PATENT APPLICATIONS

The right of foreign priority is claimed under 35 U.S.C. § 119(a) based on Federal Republic of Germany Application No. 10 2006 009 833.1, filed Mar. 1, 2006, the entire contents of which, including the specification, drawings, claims and abstract, are incorporated herein by reference. The present application also claims benefit of priority to U.S. Provisional Application Ser. No. 60/853,442, filed Oct. 23, 2006, the entire contents of which are incorporated herein by reference.

BACKGROUND OF THE INVENTION

The invention relates to a method and a microscope, in particular a laser scanning fluorescence microscope, for high spatial resolution examination of samples, the sample to be examined comprising a substance that can be repeatedly converted from a first state into a second state, the first and the second states differing from one another in at least one optical property, comprising the steps that the substance in a sample region to be recorded is firstly brought into the first state, and that the second state is induced by means of an optical signal, spatially delimited subregions being specifically excluded within the sample region to be recorded.

Methods and microscopes of the type named at the beginning are known from practice. In principle, Abbe's law sets a theoretical limit to the spatial resolution of imaging optical methods owing to the diffraction limit, the diffraction limit being a function of the wavelength of the light used. However, it is possible with the aid of the methods and microscopes discussed here to achieve spatial resolutions that are improved beyond the theoretical diffraction limits known from Abbe.

In the known methods, there are provided for this purpose in the samples to be examined substances that can be repeatedly converted from a first state into a second state, the first and the second states differing from one another in at least one optical property. In the case of most known methods, the first state is a fluorescence-capable state (named state A below), and the second state is a nonfluorescence-capable state (named state B below). After the substance in a sample region to be recorded has been brought into the fluorescence-capable state A by means of a switching signal, state B is induced in spatially limited subregions of the sample region to be recorded by means of an optical signal, and the fluorescence of fluorescence molecules is thereby suppressed. The physical process of fluorescence suppression can be of a very different nature in this case. Thus, for example, stimulated emission from the previously excited state, or an optically induced structural change in the fluorescence molecules is known.

What is decisive is that the transition induced by an optical signal from the first into the second state in the sample volume takes place in large regions in a saturated fashion, that is to say completely, and precisely does not take place in at least one subregion of the sample volume in that the optical switching signal is specifically not irradiated there. This effect can be achieved by producing an intensity zero point of the optical signal. No transition into the second state (in general the non-fluorescing state B) takes place at the zero point and in its immediate vicinity, and so the first state (in general the fluorescing state A) is retained. Even in the close vicinity of the intensity zero points, a saturation of the transition A→B owing to the optical signal leads in the illuminated regions of the sample region to be recorded to a (virtually) complete transfer into the state B. The more strongly the process is driven into saturation, that is to say the more energy that is introduced by the optical signal into the regions around the zero point, the smaller becomes the region with fluorescence molecules in the fluorescence-capable state A, or generally in a "luminous" state. This region can be rendered arbitrarily small in principle as a function of the degree of saturation in the immediate zero point vicinity. It is therefore possible to mark regions of the state A that are arbitrarily much smaller than the smallest regions of an applied optical signal that are possible on the basis of the diffraction limit. If the region of the state A is subsequently read out, for example by irradiating a test signal, the (fluorescence) measuring signal originates from a defined region that can be smaller than is permitted by the diffraction limit. If the sample is scanned point by point in the way described, an image is produced with a resolution that is better than is allowed by diffraction theory.

Methods of the type described here in the case of which the optical property of fluorescence capability/non-fluorescence capability is used as difference between two states are disclosed, for example, in DE 103 25 459 A1 and DE 103 25 460 A1. In these methods, fluorescence molecules are brought with the aid of an optical signal from a state A (fluorescence-capable) into a state B (nonfluorescence-capable), saturation being achieved in the transition A→B. The regions of the sample that remain in the fluorescence-capable state A result in each case from an intensity minimum, having a zero point, in the irradiated optical signal. The intensity minima are part of an interference pattern. The sample is scanned by displacing the intensity minima in the optical signal, the displacement being effected by shifting the phase of the interfering beams.

SUMMARY OF THE INVENTION

It is disadvantageous in the known methods that the interference pattern produced by the interfering beams and having local punctiform intensity minima can only with great difficulty be kept over a sufficiently long period in a stable state sufficient for attaining very high resolutions. This holds, in particular, when use is made of high numerical aperture optics. These can depolarize the light beams passing them and, in some circumstances, also entail phase shifts, something which can have a negative effect on the interference pattern and, in the extreme case, can even lead to a complete destruction of the interference structure.

It is now an object of the present invention to specify a method and a microscope of the type mentioned at the beginning, in accordance with which it is possible to achieve with the aid of structurally simple and cost effective means a high resolution that can be kept stable over a sufficiently long period even given the use of high numerical aperture optics.

The above object is achieved by means of a method. The method is accordingly configured and developed in such a way that the optical signal is provided in such a way that a standing wave with defined intensity zero points is formed in the sample region to be recorded.

The above object is achieved, furthermore, by a microscope. In accordance therewith, the microscope is configured and developed in such a way that the optical signal can be provided in such a way that a standing wave with defined intensity zero points is formed in the sample region to be recorded.

The method according to the invention and the microscope according to the invention can be used in a particularly advantageous way in conjunction with first and second states that are very long lasting or are even temporally stable permanently. In this case, it is possible to select for the saturation of the transition from the first into the second state a comparatively long period within which the energy of the optical signal that is required for saturation is irradiated. The local intensities relating to transitional saturation can thereby be selected to be very slight. Above all, the total energy available from a radiation source of the optical signal can be distributed over voluminous regions in the sample space, and a number of intensity zero points, or an extended zero point can be produced. The saturation can be achieved despite the low local intensities resulting therefrom in the vicinity of the zero point(s) by comparison with the application of the total signal around only one punctiform zero point. This requires that the signal be irradiated only for a sufficiently long time until all the molecules in the vicinity of the zero points are finally in the second state. This is a decisive difference from the case of a shortlived state (for example in the STED method with a typical lifetime of ~1 ns for a fluorescence-capable state A), where the energy required for saturation must be irradiated in such a short time (substantially faster than the rate A→B) that the total power of the radiation source is sufficient only to produce one (or at most some few) local zero points. It may be demonstrated for concrete systems that it is possible in the case of stable states (for example photochromic dyes) or long lived states (for example transfer into the triplet system in the case of the GSD, GSD=Ground State Depletion, method) for the power of cost effective and commercial laser systems to be distributed over such large regions that a number of punctiform intensity zero points (>>10) or entire stripes of vanishing intensity in the immediate vicinity of which saturation can be achieved as before, can be produced in the sample. This enables a parallelized imaging when the sample is simultaneously scanned with the multiplicity of punctiform zero points or with zero point lines, and the signals are detected simultaneously for each zero point in a separate fashion by a detector. In this way, it is possible to design microscopes with resolutions below the classic diffraction limit, their imaging rate being in the region of STED-based methods, and being substantially increased by comparison with systems with a single local zero point.

It is provided in a concrete embodiment in which the sample is illuminated through an objective, that at least two coherent light beams are focused into the pupil of the objective in order to produce a standing wave. It is possible in this case, for example, to produce standing waves in one direction by focusing precisely two coherent light beams into the pupil of the objective. A superposition of the standing waves in two directions can be achieved by focusing four pairwise coherent light beams into the pupil of the objective. The superposition forms a 2D grating pattern, an orthogonal superposition of the standing waves being preferred with regard to an easy evaluability, and so a chessboard pattern results.

With regard to a particularly simple construction, it is provided that the coherent light beams are focused into an intermediate image of the entrance pupil of the objective with the aid of at least one lens.

In a further embodiment, it is provided to use optical fibers via which the coherent light beams are provided. In the simplest case, these can be glass fibers, for example. The coherent light beams can be focused in a particularly simple way into the entrance pupil of the objective when the exit surfaces of the optical fibers are positioned in an intermediate image of the entrance pupil of the objective, for example. It is particularly advantageous to use polarization-maintaining optical fibers, the advantages of such a design being explained in detail further below.

Alternatively, the coherent light beams can be generated by means of a preferably holographic grating arranged in the beam path, or by means of a preferably programmable phase modulator arranged in the beam path. In order to produce very high resolution images, use is ideally made of a high numerical aperture optics that from the very first produces the smallest possible light structures within the framework of the diffraction limit. A maximum in resolution can be achieved in conjunction with high numerical aperture systems.

In a very particularly preferred embodiment, the coherent light beams are polarized only in a tangential direction of the pupil of the objective. Undesired variations in the polarization state of the light, which can occur when (linearly) polarized light is focused through an optics of high numerical aperture, can be prevented by means of these measures. If x- and y-directions define the plane of the entrance pupil, and z defines the optical axis, a light beam originally polarized in general in the x-direction, for example, can also have polarization components in the y- and z-directions after traversing the optics. This also holds in general for zero points of a standing wave in the focal space. Consequently, a light beam originally polarized in the x-direction will in some circumstances exhibit light in the y- and z-directions at the positions of the zero points of the x-component of the light. This is a function, ideally, of the position, the relative phase and of the polarization state of the light beams focused into the entrance pupil. By means of polarizing the light beams exclusively in the tangential direction of the pupil of the objective, the zero points of the standing wave are also not influenced, or are influenced only insubstantially, by the described depolarization effects of high numerical aperture objectives, and so the zero points of the standing waves are retained permanently even during scanning of the sample.

In order to scan the entire sample region to be recorded, it can be provided that the intensity zero points of the standing wave are shifted in stepwise fashion. Such a shift can be achieved, in particular, by varying the relative phase angles of the individual coherent light beams relative to one another. In a way that is particularly easy to manage, the changes in the relative phases of the individual coherent light beams can be implemented by varying the optical path length in at least one of the coherent light beams. Provided for detecting the measuring signal emanating from the sample is a detector that is, for example, designed as a CCD detector, an EMCCD detector or as an APD (Avalance Photodiode) array. The readout operation of the detector is advantageously synchronized with the scanning operation, for example in such a way that the detector is read out after each scanning step.

Laser light sources, however, can be used to generate the light beams. Alternatively, it is conceivable to use white light sources, in which case the coherence length of the light source must be sufficiently short. In the case of white light sources, use is advantageously made of retroreflectors that can be adjusted and with the aid of which a wavelength compensation can be carried out between pairwise coherent light beams.

With regard to a high measure of flexibility, it is provided to use additional light sources whose light can, on the one hand, be coupled into the beam path in order to switch the substance back from the second state into the first state and/or to read out the first states in the beam path. By contrast with punctiform illumination, which is selected in the case of the optical signal for implementing a standing wave, the additional light sources are preferably used such that they illuminate the field of view over a large area. In concrete applications, for example when examining living cells that serve for imaging biological processes in the vicinity of the cell membrane, the first states can be read out in the TIRF (Total Internal Reflectance Fluorescence) mode. To this end, the standing waves can be formed as evanescent fields such that the standing wave is effective only in a very thin layer of the sample owing to the penetration depth being delimited by total reflection. Processes in the vicinity of the cell membrane of living cells in this way can be visualized with very high spatial resolution.

There are various possibilities of configuring and developing the teaching of the present invention in an advantageous way. To this end, reference is to be made, on the one hand, to the subordinate claims and, on the other hand, to the subsequent explanation of preferred exemplary embodiments of the method according to the invention and the microscope according to the invention for high spatial resolution examination of samples.

BRIEF DESCRIPTION OF THE DRAWINGS

Preferred refinements and developments of the teaching are also explained in general in conjunction with explanations of the preferred exemplary embodiments and with the aid of the drawing, in which.

DETAILED DESCRIPTION OF THE PREFERRED EMBODIMENTS

Figure 1:
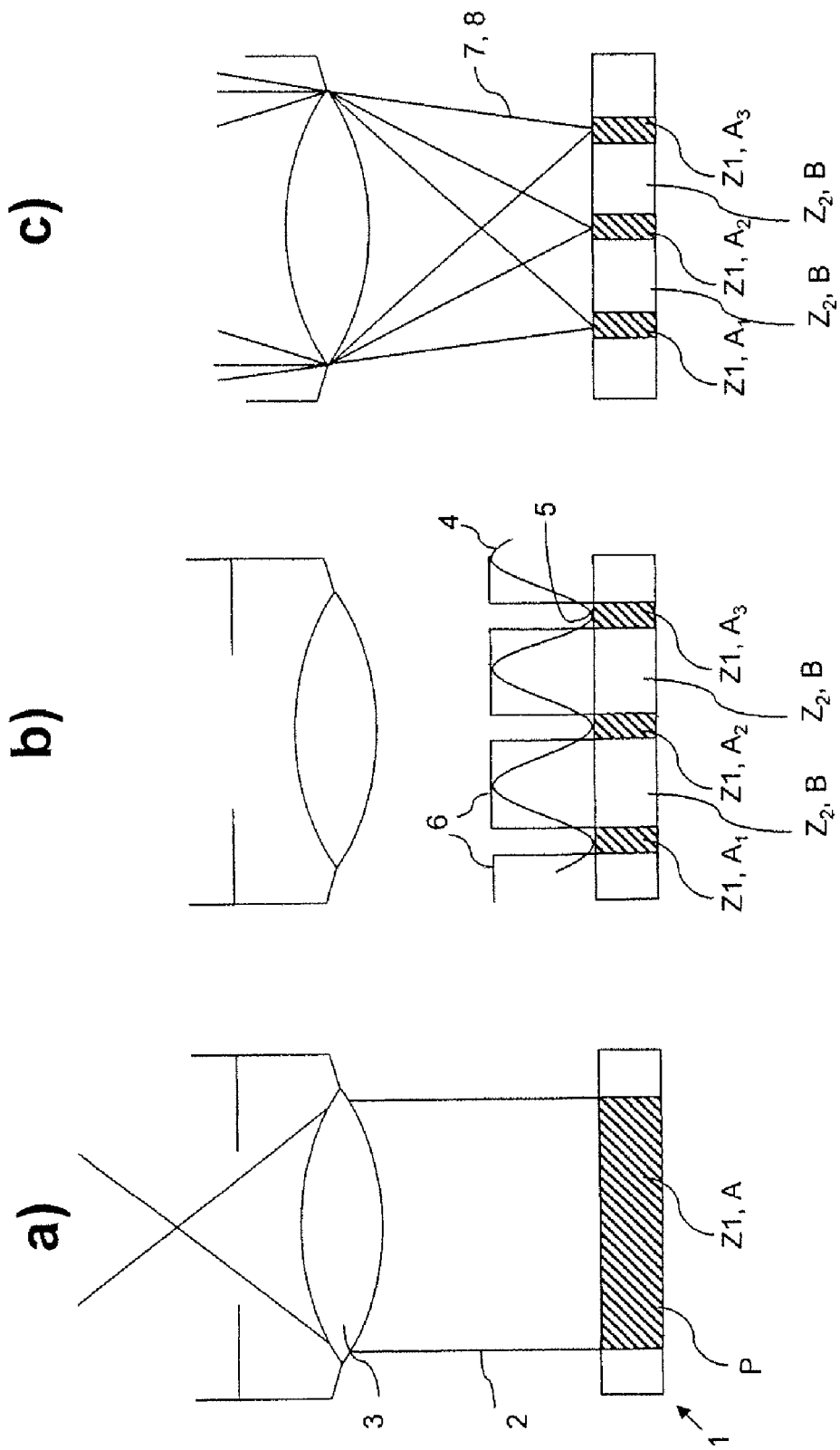
FIG. 1 shows a schematic of a cyclic illumination scheme of a method for high spatial resolution examination of samples.

FIG. 1 shows a schematic of a cyclic illumination operation such as is used for high spatial resolution examination of samples beyond the diffraction limited resolving limit. In accordance with FIG. 1a, the first step is to use a switching signal 2 to bring into the first state Z1 in the entire sample space P to be recorded a substance that is provided in the sample 1 and can be converted repeatedly from a first state Z1 into a second state Z2, the first and the second states Z1, Z2 differing from one another in at least one optical property. In the exemplary embodiment illustrated in concrete terms, the first state Z1 is a fluorescing state A, and the second state Z2 is a non-fluorescing state B. In the example illustrated in concrete terms, the substance provided in the sample 1 is a photochromic substance whose molecules are brought into the fluorescence-capable state A by irradiation with light of a first wavelength, the switching signal 2. This happens ideally in that the sample 1 is irradiated in the entire sample space P by illumination through an objective 3 with the aid of the switching signal 2.

In the case of ground state depletion (GSD), the transition into the fluorescence-capable (singlet) state usually takes place spontaneously. The irradiation of optical switching signals is therefore superfluous in this case, there being a need only to take account of waiting times of typically 1 to 100 μs (in part also a little longer).

In a next step—illustrated in FIG. 1b—light of another wavelength, the so-called optical signal 4, is applied to the sample region P to be recorded. This happens in the form of a light structure with defined intensity zero points 5. The optical signal 4 induces in a saturated fashion the transition A→B in all regions 6 illuminated with the light of the optical signal 4. In other words, it is only regions of the substance that are narrowly defined in the immediate vicinity of the intensity zero points 5 that remain in state A. The remaining regions $A_1$, $A_2$, $A_3$, . . . of the substance in state A can be much smaller than the dimensions of the light structure of the optical signal 4 itself, that is to say, in concrete terms, much smaller than diffraction-limited structures. The size of the regions $A_1$, $A_2$, $A_3$, . . . remaining in state A is determined entirely as a function of the quality of the intensity minima 5, and thus of the degree of saturation of the transition A→B that is achieved. In FIG. 1c is a schematic of the readout operation of state A. To this end, an optical test signal 7 is irradiated into the sample region P to be recorded in such a way that those regions prepared in accordance with FIG. 1b and in which the substance has remained in state A, are recorded. Regions of the substance possibly still existing in state A that lie outside the sample region P to be recorded may not be recorded in this case. The fluorescent light emanating from the substance in state A is detected as measuring signal 8 by a detector (not shown), a unique assignment of the detected measuring signals 8 to the individual regions $A_1$, $A_2$, $A_3$, . . . being undertaken.

The cycle illustrated in FIGS. 1a to c is repeated, the standing wave pattern being shifted somewhat further upon each repetition. It is possible in this way for the entire sample region to be recorded to be imaged with a resolution in the subdiffraction range.

Figure 2:
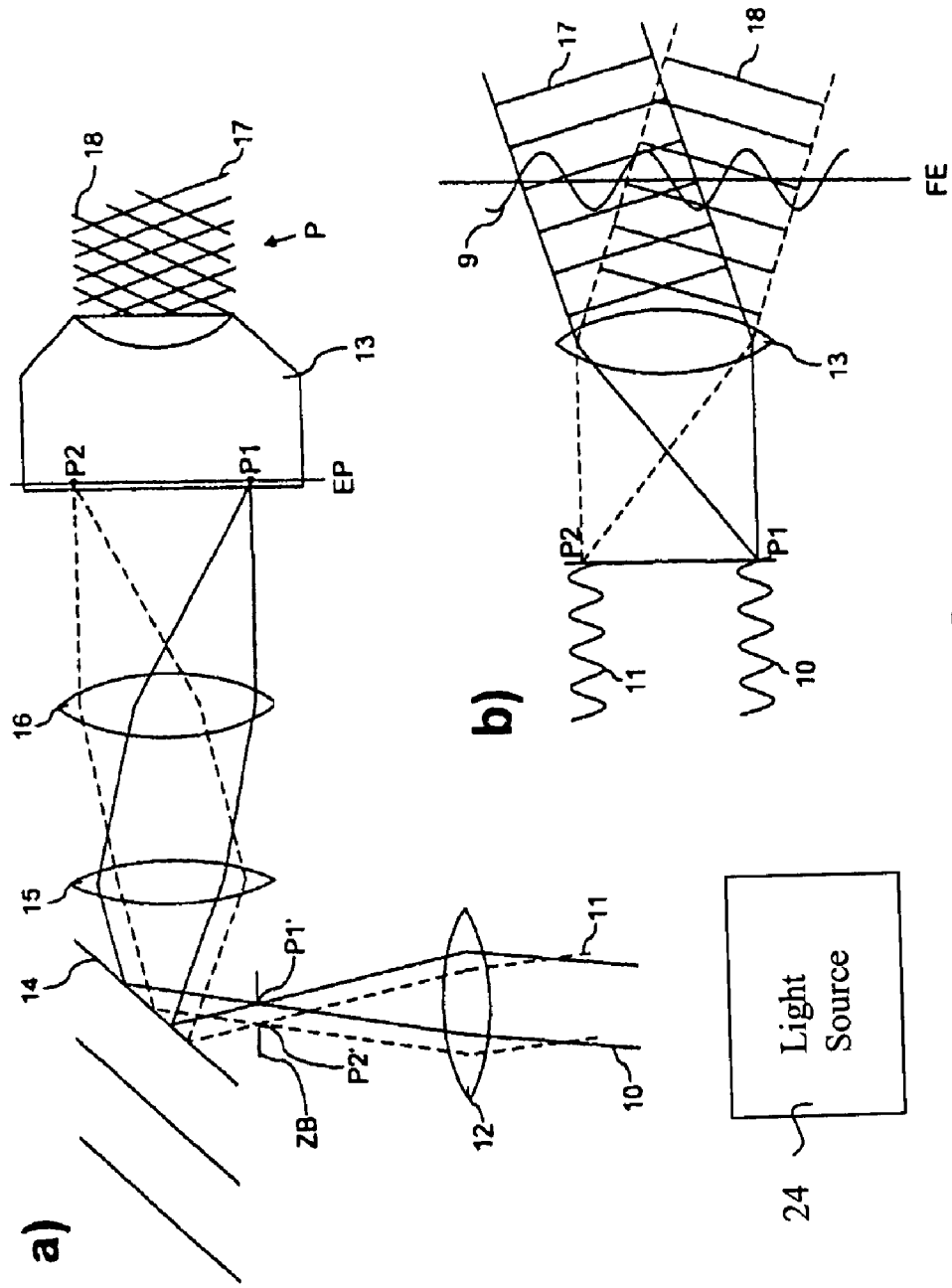
FIG. 2 shows a schematic of an exemplary embodiment of an inventive microscope.

FIG. 2 is a schematic of an exemplary embodiment of an inventive microscope with a standing wave 9 in the sample region P. In accordance with the illustration in FIG. 2a, to this end two coherent light beams 10, 11 are focused by means of, an optical element, a lens 12 into an intermediate image ZB of the entrance pupil EP of the objective 13. The light beams 10, 11 are generated by a light source 24, as shown in FIG. 2. As an alternative to the lens 12, the optical element which provides the coherent light beams to the intermediate image ZB of the entrance pupil may be optical fibers or a programmable phase modulator as discussed above. For reasons of clarity, one of the two coherent light beams 10 is illustrated by a continuous line, and the other light beam 11 is illustrated by a dashed line. In other words, in the exemplary embodiment illustrated the focusing of the coherent light beams 10, 11 is selected such that the focal points P1', P2' are formed in the intermediate image ZB. In principle, the focusing can be performed not only into the intermediate image ZB, but also directly into the image or into an arbitrary plane conjugate thereto. The two coherent light beams 10, 11 are coupled into the beam path of the microscope via a beam splitter 14. Via the scanning eyepiece 15 and the tube lens 16, the two beams 10, 11 are imaged into the entrance pupil EP such that the two focal points P1, P2 result there.

As indicated in FIG. 2a, the light of further light sources can be coupled in via the beam splitter 14, for example the switching signal 2 or the test signal 7. The measuring signals 8 can also be guided to a detector (not shown) via the beam splitter 14.

As illustrated in detail in FIG. 2b, two plane waves 17, 18 are formed in the sample region P as a consequence of the described focusing of the two coherent light beams 10, 11 in the entrance pupil EP of the objective 13. The standing wave 9 illustrated in FIG. 2b is formed with defined intensity zero points in the focal plane FE owing to interference between the two plane waves 17, 18.

Figure 3:
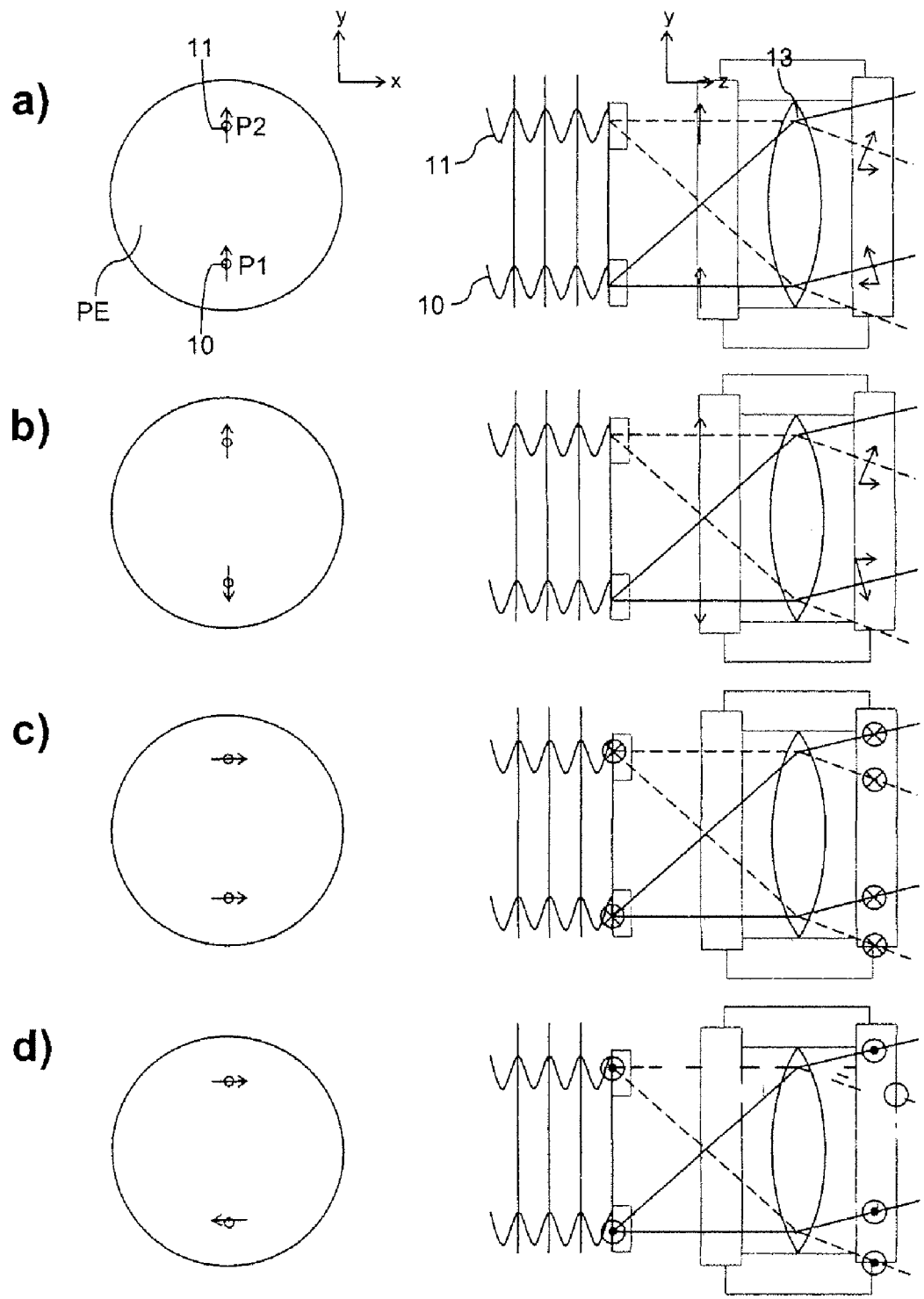
FIG. 3 shows a schematic of different variants of the focusing of coherent light beams into the entrance pupil of the objective together with various polarization states.

FIG. 3 is a schematic of different polarization states of the coherent light beams 10, 11 focused into the pupil plane PE, and of the polarization states, resulting therefrom in each case, of the standing waves 9 in the sample region P. As already set forth, scanning of the sample 1 by means of shifting the standing wave 9 perpendicular to its traveling direction is achieved by virtue of the fact that the relative phase of the two light beams 10, 11 in the focal points P1 and P2 is varied. The case of linearly polarized light in the y-direction is illustrated in FIGS. 3a and b, the points P1 and P2 being offset in the y-direction. FIGS. 3c and d show the case of linearly polarized light in the x-direction, the points P1 and P2 being offset in the y-direction. Illustrated respectively in this case are the cophasal cases (FIGS. 3a and c), in which the wave packets oscillate synchronously, and the antiphasal cases (FIGS. 3b and d) in which the wave packets oscillate asynchronously. The different polarization states are described below only with reference to the example of these two concrete phase angles. By contrast, continuous shifting of the intensity zero points of the standing wave 9 in the focal plane FE also requires further phase angles to be generated therebetween in discrete steps.

The polarization directions of the light waves are tilted by strongly focusing objectives/lenses 13 during traversal of the coherent light beams 10, 11. This is illustrated respectively in the right-hand constituent images of FIG. 3. In the case of the light polarized in the y-direction (FIGS. 3a, b), polarization components are produced in the z-direction. These are antiphasal in the case shown in FIG. 3a, that is to say they interfere negatively, and no light with z-polarization is produced, in effect. For beams that do not lie on the optical axis, however, a z-component is already generally produced here. This means that although the intensity zero points exhibit a zero point with reference to the original polarization (in the y-direction), they generally include, however, a finite fraction of z-polarized light.

This becomes clearer in the case illustrated in FIG. 3b. Here, the tilting of the polarization vectors, and the antiphasal position of the coherent light beams 10, 11 lead to a depolarization in the z-direction, the coherent light beams 10, 11 interfering positively in the z-direction, and therefore having a clearly expressed z-component. This is stronger the larger the focusing angle of the objective 13. Since the light beams 10, 11 are to be deflected at as large an angle as possible in order to produce a standing wave 9 with narrow minima, it follows that this arrangement cannot be used.

Preference is to be given to an arrangement such as is illustrated in FIGS. 3c and d. In these cases, the focal points P1 and P2 are offset in the y-direction, and the polarization is selected in the x-direction. No depolarization takes place here during focusing—even by means of a high numerical aperture optics 13—that is to say the light continues to be polarized in the x-direction even in the focal space. No destruction of the intensity zero points of the standing wave 9 by means of other polarizations takes place. This holds for all phase angles, and thus for any desired position of the zero points in the focal space. Consequently, the conditions illustrated in FIGS. 3c and d are very particularly suitable to serve as an optical signal 4 for the saturated transition from the first state A into the second state B. What is decisive in any event is that only polarization vectors with a pure tangential component occur in the entrance pupil EP and radial components, which depolarize strongly in the z-direction, are avoided. The intensity zero points are then retained in all polarization directions even when the standing wave pattern 9 is scanned at will through the sample 1.

For light beams that do not lie on the optical axis, by contrast, the conditions are somewhat more complicated. In these cases, slight depolarization effects occur even given purely tangential polarization. However, it may be shown by calculations for realistic conditions that the fraction of the depolarized light in such cases is of the order of magnitude of $10^{-3}$ to $10^{-2}$ in an arrangement in accordance with FIGS. 3c and d, which is sufficiently low. In the case of an arrangement in accordance with FIGS. 3a and b, by contrast, the z-component of the polarization, in particular, is typically of the same order of magnitude as the original polarization, and is even larger, in part, as a result of which the zero points would be completely destroyed.

Figure 4:
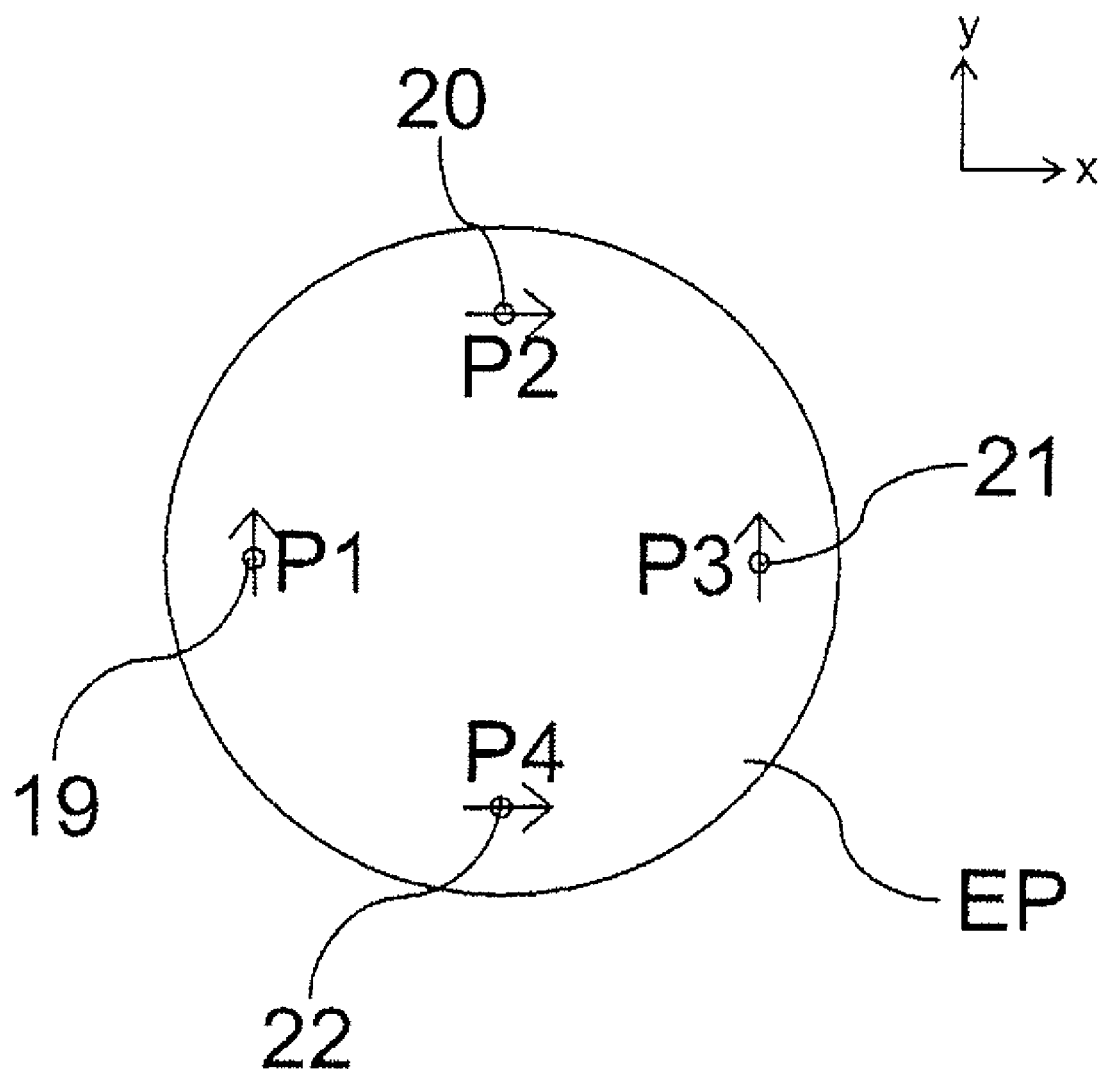
FIG. 4 shows a schematic of an exemplary embodiment having a total of four pairwise coherent light beams.

FIG. 4 shows an exemplary embodiment having a total of four light beams of which in each case two are pairwise coherent. Specifically, what is shown is the entrance pupil EP with the four focal points P1 to P4. The light beams 19-22 exhibit exclusively polarization vectors with tangential components, and this is indicated by the arrows illustrated. The two focal points P1 and P3 offset in the x-direction, that is to say the light beams 19 and 21, are mutually coherent and exhibit a polarization in the y-direction. The result of this is a 2D line pattern in the focal plane FE with well preserved intensity zero points. The two light beams 20 and 22 with the focal points P2 and P4 are likewise mutually coherent and exhibit a polarization in the x-direction such that the resulting line pattern is rotated by 90° and polarized in the x-direction. Consequently, the two resulting line patterns do not interfere with one another, but rather this leads to a simple addition of the intensity values. The result is consequently a two-dimensional grating pattern with periodically occurring intensity zero points. The latter can be shifted in the x-direction during scanning of a sample by varying the relative phases of the coherent light beams 19, 21 with the focal points P1 and P3. The zero points can be shifted in the y-direction by varying the relative phase of the coherent light beams 20, 22 with the focal points P2 and P4.

In order to avoid repetitions, reference may be made to the general part of the description and to the attached patent claims with regard to further advantageous refinements of the method according to the invention and of the microscope according to the invention.

Finally, it may be pointed out expressly that the above-described exemplary embodiments serve merely for discussing the teaching claimed, but do not restrict the latter to the exemplary embodiments.

The invention claimed is:

1. A method for high spatial resolution examination of a sample, the sample to be examined comprising a substance that can be repeatedly converted from a first state into a second state, the first and the second states differing from one another in at least one optical property, comprising:
   bringing a sample region of the substance to be recorded into the first state; and
   inducing the second state using an optical signal, wherein spatially delimited subregions are specifically excluded within the sample region to be recorded by the inducing,
   wherein the optical signal is provided in such a way that a standing wave with defined intensity zero points is formed in the sample region to be recorded,
   the sample being illuminated by an objective, wherein at least two coherent light beams are focused into the entrance pupil of the objective in order to produce a standing wave,
   wherein standing waves are superposed in two directions by focusing four pairwise coherent light beams into the entrance pupil of the objective.

2. The method as claimed in claim 1, wherein the standing waves are superposed in an orthogonal fashion to one another.

3. The method as claimed in claim 1, wherein the coherent light beams are generated by a laser light source.

4. The method as claimed in claim 1, wherein the coherent light beams are generated by a white light source of short coherence length.

5. The method as claimed in claim 1, wherein the coherent light beams are focused into an intermediate image of the entrance pupil of the objective with the aid of at least one lens.

6. The method as claimed in claim 1, wherein the coherent light beams are provided by optical fibers.

7. The method as claimed in claim 6, wherein the exit surfaces of the optical fibers are positioned in an intermediate image of the entrance pupil of the objective.

8. The method as claimed in claim 6, wherein the optical fibers are polarization maintaining.

9. The method as claimed in claim 1, wherein the coherent light beams are generated by a holographic grating.

10. The method as claimed in claim 1, wherein the coherent light beams are generated by a programmable phase modulator.

11. The method as claimed in claim 1, wherein a high numerical aperture optics is used as the objective.

12. The method as claimed in claim 1, wherein the coherent light beams are polarized only in a tangential direction of the entrance pupil of the objective.

13. The method as claimed in claim 1, wherein the intensity zero points are shifted relative to one another by varying the relative phases of the coherent light beams.

14. The method as claimed in claim 13, wherein an optical path length is varied in at least one of the light beams in order to change the relative phases of the coherent light beams in relation to one another.

15. The method as claimed in claim 1, wherein light is provided for switching the substance back from the second state into the first state and/or for reading out first states.

16. A microscope for high spatial resolution examination of a sample, the sample to be examined comprising a substance that can be repeatedly converted from a first state into a second state, the first and the second states differing from one another in at least one optical property, the microscope comprising:

a microscope objective arranged to illuminate the sample;

an illuminating light source arranged to generate illuminating light beams; and an optical element arranged to receive the illuminating light beams and provide four pairwise coherent light beams at an intermediate image of an entrance pupil of the microscope objective in order to produce standing waves with defined intensity zero points formed in a sample region to be recorded, the standing waves superposed in two directions.

17. The microscope as claimed in claim 16, wherein the microscope objective has a high numerical aperture.

18. The microscope as claimed in claim 16, wherein the illuminating light source is designed as a laser light source.

19. The microscope as claimed in claim 16, wherein the illuminating light source is designed as a white light source of short coherence length.

20. The microscope as claimed in claim 16, wherein the optical element is at least one lens arranged to focus the coherent light beams into the intermediate image of the entrance pupil of the microscope objective.

21. The microscope as claimed in claim 16, wherein the optical element comprises polarization-maintaining optical fibers, the exit surfaces of the optical fibers being arranged in the intermediate image of the entrance pupil of the microscope objective.

22. The microscope as claimed in claim 16, wherein the optical element comprises a programmable phase modulator arranged in the beam path in order to generate the coherent light beams.

23. The microscope as claimed in claim 22, wherein the phase modulator is designed as a liquid crystal.

24. The microscope as claimed in claim 16, wherein light of at least one additional illuminating light source is provided for switching the substance back from the second state into the first state and/or for reading out the first states.

25. The microscope as claimed in claim 24, wherein the at least one additional illuminating light source illuminates a field of view over a large area.

26. The microscope as claimed in claim 16, wherein the first states are read out in the total internal reflection fluorescence (TIRF) mode, the standing waves being formed as evanescent fields.

27. The microscope as claimed in claim 16, wherein the microscope is a laser scanning fluorescence microscope.

* * * * *